US008944601B2

(12) United States Patent
Muehlhoff et al.

(10) Patent No.: US 8,944,601 B2
(45) Date of Patent: Feb. 3, 2015

(54) CONTACT GLASS FOR OPHTHALMIC SURGERY

(75) Inventors: Dirk Muehlhoff, Kunitz (DE); Elke Ebert, Jena (DE); Karsten Festag, Jena (DE); Uwe Wolf, Magdala (DE); Dirk Preuss, Jena (DE); Mark Bischoff, Bad Berka (DE); Gregor Stobrawa, Jena (DE); Dietmar Steinmetz, Bucha (DE); Steffen Dubnack, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 1292 days.

(21) Appl. No.: 12/064,575

(22) PCT Filed: Aug. 25, 2006

(86) PCT No.: PCT/EP2006/008360

§ 371 (c)(1), (2), (4) Date: Feb. 22, 2008

(87) PCT Pub. No.: WO2007/022993

PCT Pub. Date: Mar. 1, 2007

(65) Prior Publication Data

US 2008/0234707 A1 Sep. 25, 2008

(30) Foreign Application Priority Data

Aug. 25, 2005 (DE) ......................... 10 2005 040 337
Aug. 25, 2005 (DE) ......................... 10 2005 040 338

(51) Int. Cl.
*A61B 3/00* (2006.01)
*A61F 9/008* (2006.01)
(Continued)

(52) U.S. Cl.
CPC ............. *A61F 9/00827* (2013.01); *A61F 9/009* (2013.01); *A61B 2019/4826* (2013.01);
(Continued)

(58) Field of Classification Search
CPC .......... A61F 2009/00872; A61F 9/008; A61B 3/125; A61B 3/117
USPC .................... 606/4, 5, 166; 128/898; 351/219
See application file for complete search history.

(56) References Cited

U.S. PATENT DOCUMENTS 4,718,418 A 1/1988 L'Esperance, Jr.
5,108,412 A 4/1992 Krumeich et al.

(Continued)

FOREIGN PATENT DOCUMENTS

DE 103 49 297 A1 5/2005
DE 103 53 264 A1 6/2005

(Continued)

OTHER PUBLICATIONS

*Intralase Product Leaflet*, Essential Technology for Biomechanical Stability, Intralase Corp., 6 pgs. (2006).

*Primary Examiner* — William Thomson
*Assistant Examiner* — Jeffrey Lipitz
(74) *Attorney, Agent, or Firm* — Patterson Thuente Pedersen, P.A.

(57) ABSTRACT

The invention relates to a contact glass for ophthalmic surgery. Said glass comprises a lens body that is held in a frame and a front lens surface that is designed to be placed against the eye. According to the invention, the front lens surface is concave and follows a surface curvature (K) and an annular gap is formed at the edge of the front lens surface between the lens body and the frame, said gap being used to apply a negative pressure in order to fix the contact glass to the eye. The frame is designed to follow the contour of an imaginary continuation of the surface curvature (K), or at least does not project beyond the latter.

29 Claims, 4 Drawing Sheets

(51) Int. Cl.
*A61F 9/009* (2006.01)
*A61B 19/00* (2006.01)

(52) U.S. Cl.
CPC . *A61B2019/4873* (2013.01); *A61B 2560/0276* (2013.01); *A61B 2562/08* (2013.01); *A61F 2009/00872* (2013.01)
USPC .................................... 351/219; 606/4; 606/5

(56) References Cited

U.S. PATENT DOCUMENTS

| | | | |
|---|---|---|---|
| 5,336,215 A | 8/1994 | Hsueh et al. | |
| 5,549,632 A | 8/1996 | Lai | |
| 5,772,675 A | 6/1998 | Hellenkamp | |
| 5,963,301 A * | 10/1999 | Volk | 351/219 |
| 5,984,916 A | 11/1999 | Lai | |
| 6,254,595 B1 | 7/2001 | Juhasz et al. | |
| 6,623,476 B2 | 9/2003 | Juhasz et al. | |
| 2001/0021844 A1 | 9/2001 | Kurtz et al. | |
| 2002/0103482 A1 | 8/2002 | Scholler et al. | |
| 2004/0220602 A1 | 11/2004 | Deng et al. | |
| 2006/0129140 A1 | 6/2006 | Todd et al. | |
| 2006/0210277 A1 | 9/2006 | Dubnack et al. | |
| 2006/0232426 A1 * | 10/2006 | Sabeta | 340/572.8 |
| 2007/0010803 A1 | 1/2007 | Bischoff et al. | |
| 2007/0237620 A1 | 10/2007 | Mühlhoff et al. | |
| 2007/0253083 A1 | 11/2007 | Muhlhoff et al. | |

FOREIGN PATENT DOCUMENTS

| | | | |
|---|---|---|---|
| EP | 1 159 986 | A2 | 12/2001 |
| EP | 1 199 046 | A2 | 4/2002 |
| WO | WO 02/083018 | A1 | 10/2002 |
| WO | WO 03/002008 | A1 | 1/2003 |
| WO | WO 2005/039462 | A1 | 5/2005 |

* cited by examiner

Fig. 3
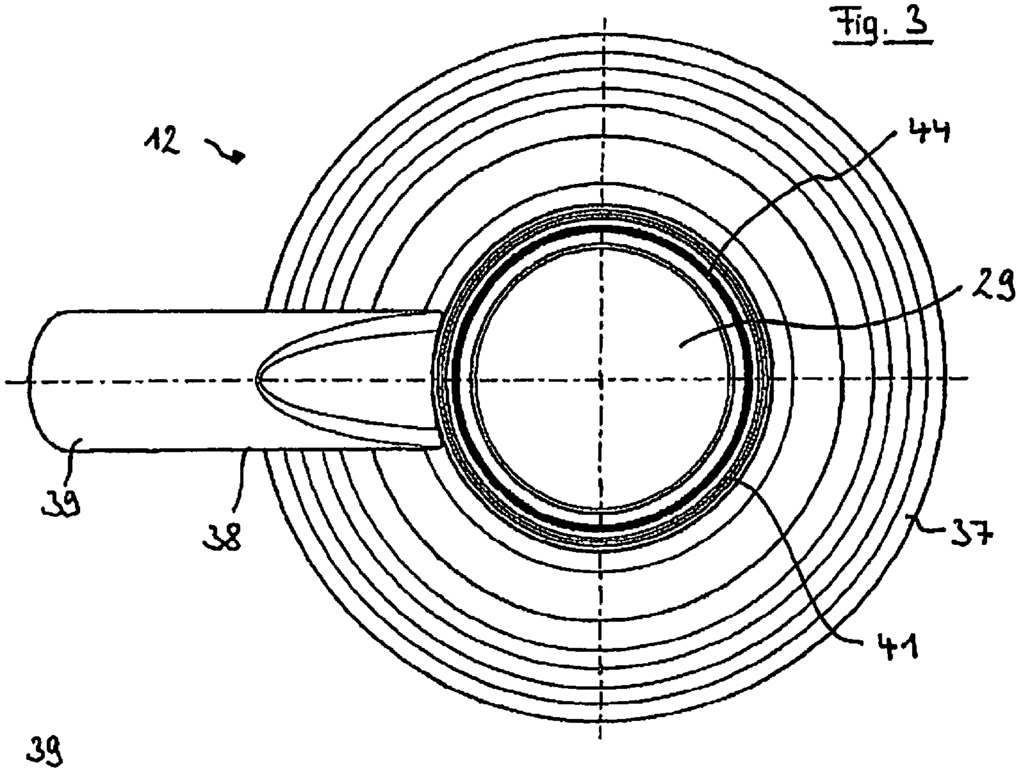
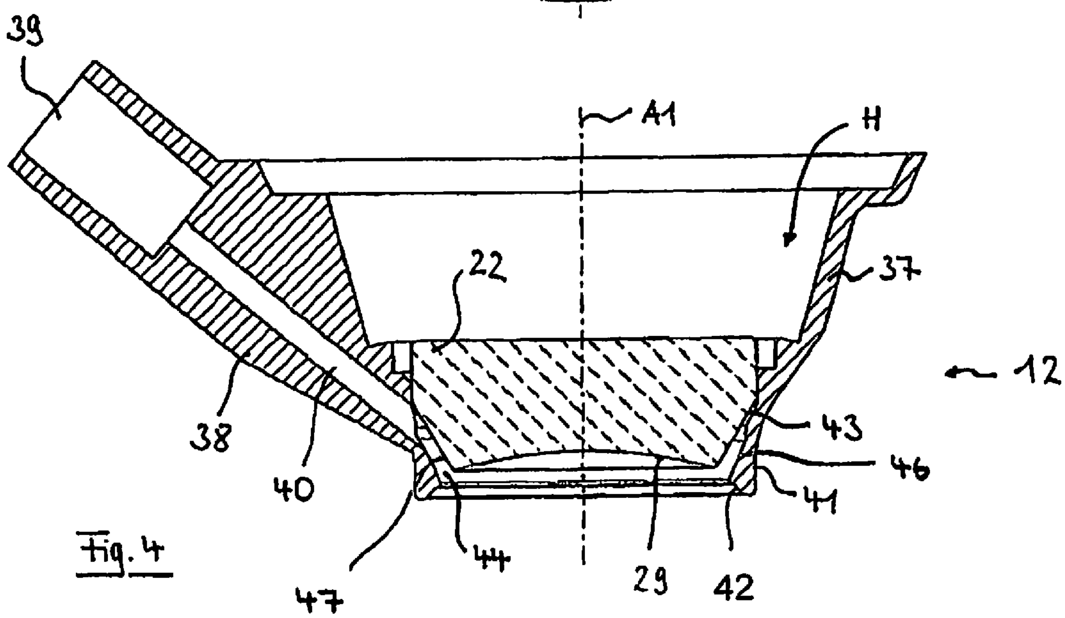
Fig. 4

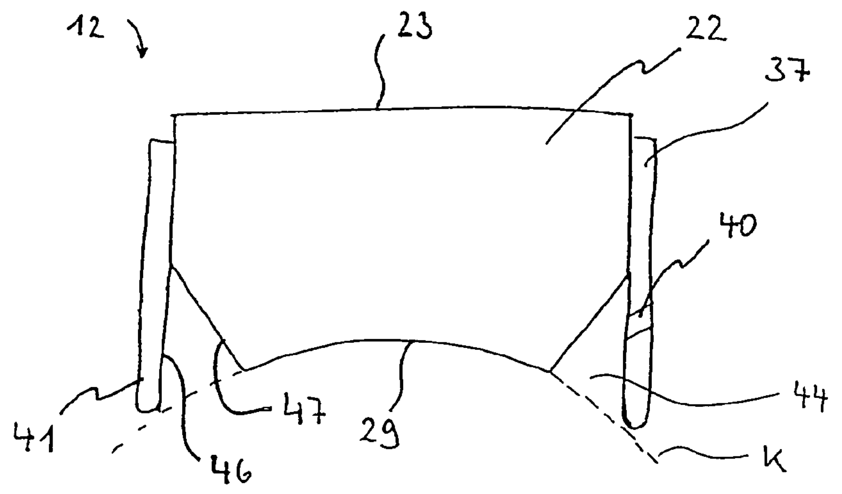
Fig. 5
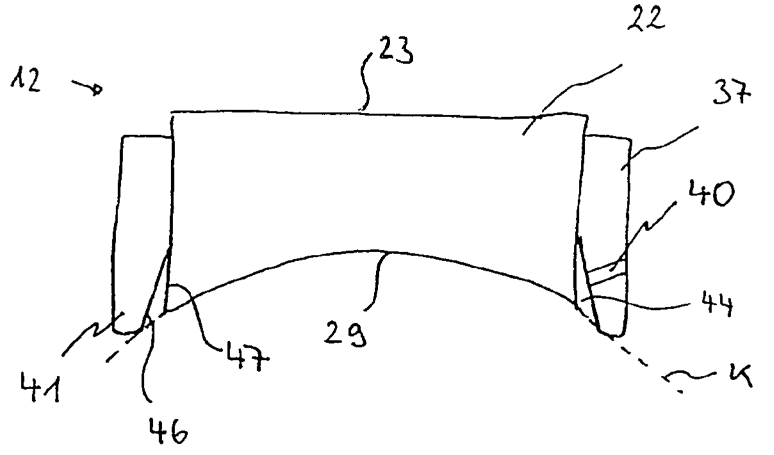
Fig. 6
Fig. 7
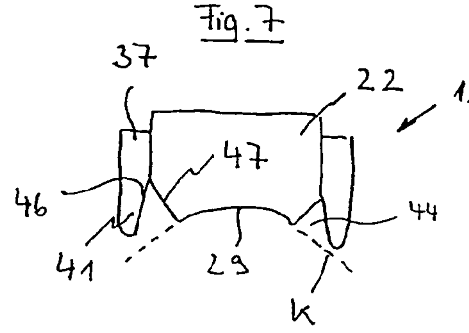
Fig. 8
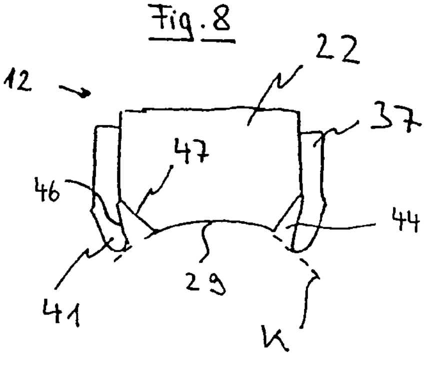

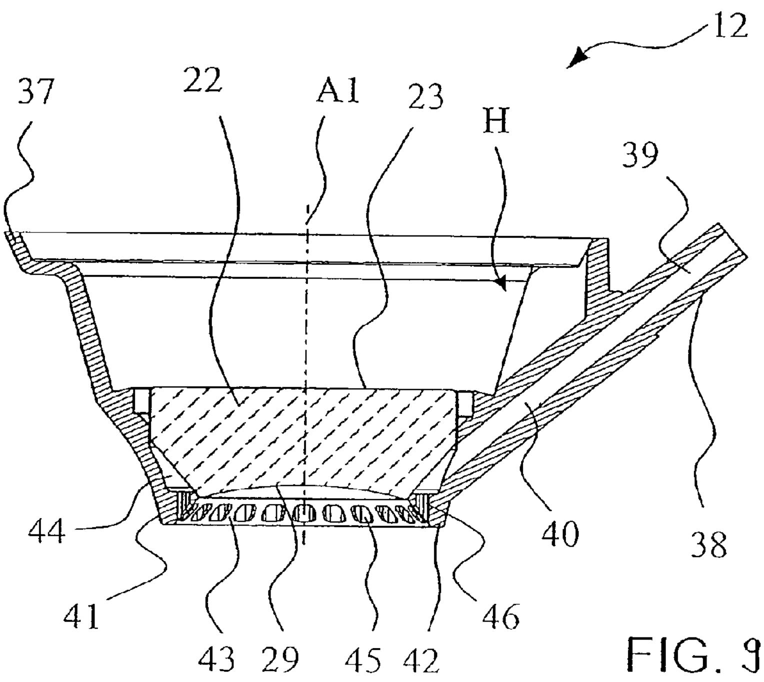
FIG. 9
FIG. 10
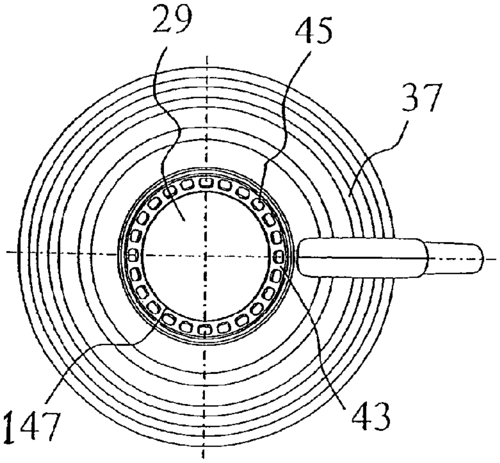
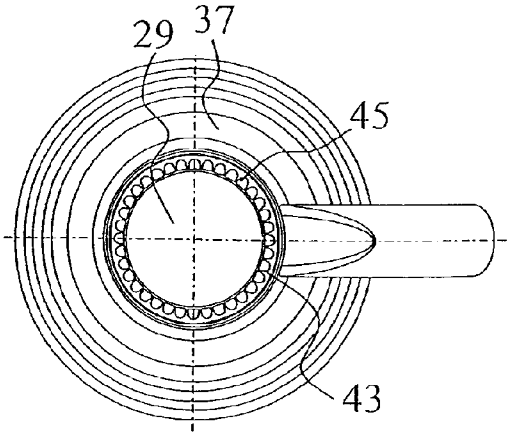
FIG. 11

CONTACT GLASS FOR OPHTHALMIC SURGERY

FIELD OF THE INVENTION

The invention relates to a contact glass for ophthalmic surgery, which glass comprises a anterior lens surface provided for placement onto the eye and means for fixing the contact glass to the eye by vacuum.

Such contact glass is shown in WO 2005/048895 A1, which otherwise deals with fixing the contact glass to a laser treatment device.

BACKGROUND OF THE INVENTION

Contact glasses in ophthalmic surgery are examples of adapters which mechanically couple the laser processing device to an object. Such coupling is required because the precision with which the laser beam is positioned in the object usually determines the precision achieved in processing. Only exact three-dimensional positioning of the laser beam in the processing volume, for example in the cornea of the eye, allows high-precision processing. Therefore, fixation of the object to be processed is effected via an adapter ensuring a precisely defined position of the object, for example of the eye, relative to the laser processing device. The adapter, which is usually referred to as contact glass, is thus part of the beam path. If the exact external shape of the object to be processed is not known, the adapter at least also functions to give the object, if possible, a certain shape which is predefined when applying a laser beam.

Since the anterior surface of the human eye's cornea varies from patient to patient, an adapter in the form of a contact glass is regularly provided in laser-assisted ophthalmic surgery. US 2001/0021844 A1 describes a corresponding contact glass which not only fixes the eye, but also deforms the anterior surface of the cornea. The US publication proposes to apply a vacuum between the cornea and the contact glass provided as a lens body, by which vacuum the eye's cornea is drawn towards the contact glass. With the lens body and the eye's cornea fixed by vacuum in this manner, the eye's cornea automatically assumes the shape of the lens body's anterior surface (anterior surface with respect to the patient). However, this type of fixing is rather inconvenient for the patient, in particular when using the barb-shaped projections provided at the bottom surface of the lens body mount according to one embodiment of US 2001/0021844 A1, said projections being intended to achieve improved fixing of the contact glass to the eye.

SUMMARY OF THE INVENTION

Therefore, it is an object of the invention to further embody a contact glass of the above-mentioned type such that secure fixing of the lens body to the eye and reliable deformation of the cornea are effected as gently as possible for the patient.

According to the invention, this object is achieved by a contact glass of the type mentioned above, wherein the anterior lens surface is annularly surrounded by an annular gap, which does not protrude with respect to an imaginary extension of the anterior lens surface, or by a multiplicity of suction orifices, through which gap/orifices a vacuum acts on the eye.

Thus, the eye's cornea is placed in contact with the anterior surface of the lens, or held against it, by mechanical pressure, said mechanical pressure resulting from suction of the eye's cornea effected in a ring-shaped region surrounding the anterior surface of the lens. The ring-shaped region comprises suction orifices which apply the vacuum. This approach has essential advantages. First, the vacuum can be applied to the eye's cornea as gently as possible. Moreover, according to an embodiment it is excluded that the eye's cornea is sucked in a ring shape into an annular gap. This also prevents undesired occlusion of the suction channel. On the other hand, the patient side of the contact glass can be substantially smooth; the eye is pressed against a smooth surface provided with suction orifices. This prevents sharp edges acting on the eye, and the complicated production method required in the prior art in order to avoid sharp edges at a suction ring is now eliminated. Thus, the invention provides a contact glass for ophthalmic surgery, which contact glass comprises a lens body, which is received in a mount and has a concave anterior lens surface designed to be placed on the eye, there being formed, at the periphery of the anterior lens surface between the lens body and the mount, an annular gap or ring-shaped region which, together with the contacted eye, acts as a suction channel via which the vacuum for fixing the contact glass to the eye can be applied, and the mount does not protrude with respect to an imaginary extension of the anterior lens surface. Together with the contacted eye, the annular gap or ring-shaped region forms a mostly air-tight chamber, allowing a force to be applied for fixing the contact glass to the eye's cornea by a vacuum.

The object is achieved, for example, by a contact glass of the above-mentioned type, wherein the mount is formed such that the suction channel between the annular gap and the eye is not yet closed when the eye is in full-surface contact with the anterior lens surface.

In contrast to the approach described in US 2001/0021844 A1, the eye's cornea is, thus, not sucked directly onto the anterior lens surface by a vacuum, but contacts the anterior lens surface due to mechanical pressure. Since the mount is provided such that the suction channel between the annular gap and the eye still remains open (i.e. the eye's cornea does not yet cover the annular gap) when the eye is in full contact with the anterior lens surface, exact mutual aligning of the contact glass and the eye can be effected. Only if the contact glass is pushed further towards the eye does the eye's cornea cover the annular gap, so that the suction channel between the annular gap and the eye is closed and the fixation by vacuum becomes active. Thus, the vacuum applied in the annular gap only serves to fix the eye, but does not directly cause the eye's cornea to deform. This makes the entire process of contacting and fixing easier to control.

The vacuum applied through the suction channel only serves to fix the eye's cornea, but does not directly cause the eye's cornea to deform, because no vacuum acts between the anterior surface of the lens and the eye's cornea. Thus, the contact glass according to the invention is particularly suitable for patients with corneal damage, anomalies or even cuts from previous ophthalmic operations that never healed in the region of the cornea to be placed in contact with the anterior surface of the lens. Since there is no vacuum acting in this region of the eye's cornea, a damaging effect can now be excluded when fixing the contact glass.

Thus, on the patient's side, the transition between the anterior lens surface and the mount is smooth (except for the annular gap); beyond the annular gap, the mount does not constitute a discontinuity.

The mount has a geometric design such that the eye's cornea, in a state where the eye is already in full-surface contact with the anterior lens surface, does not yet contact the edge of the mount which limits the annular gap and, as a consequence, does not yet close the annular gap to the suction channel. This may be achieved, for example, in that the axially foremost contour of the mount does not protrude, or even recedes, with respect to a curved surface which the eye's cornea has when the eye fully contacts the anterior lens surface. The shape of the curved surface depends substantially on the state which the eye has when it fully contacts the anterior lens surface.

A simple design also allows to refer the curved surface, with respect to which the axially foremost contour of the mount does not protrude or even recedes, to the curvature of the anterior lens surface, so that the axially foremost contour of the mount will then not protrude or will even recede with respect to the imaginary extension of the anterior lens surface.

The contact glass according to the invention allows the natural shape of the cornea to be maintained with the contact glass placed thereon, which is particularly convenient for the patient. The eye is placed in contact with the contact glass at a suitable radius of curvature with minimal deformations.

Particularly simple manufacture is achieved if the annular gap is formed by one or more frustoconical surfaces or conical surfaces, respectively, on the mount and/or on the lens body. Moreover, a further embodiment is easily realized by such conical surfaces as a rule, wherein the annular gap tapers away from the eye and, in particular, tapers off at an acute angle of less than or equal to ninety degrees at the end facing away from the eye.

Such design of the annular gap is further advantageous, because it effectively prevents parts of the eye's cornea from being sucked into the upper region of the suction channel and thereby partially clogging it. As a consequence, introduction of the vacuum into the annular gap is uncritical then, because the entire annular gap is always effective as a suction channel and, in particular, the vacuum connector cannot be occluded by the eye's cornea.

The contact glass according to the invention enables particularly easy placement of the contact glass onto the eye's cornea, in particular if the curved surface of the anterior lens surface has a slightly flatter curvature than the eye's cornea. When approaching the contact glass, only the central region of the eye's cornea, i.e. the corneal vertex, touches the anterior lens surface. As placement progresses, the eye's cornea gradually contacts the full anterior lens surface, with the suction channel still not being closed in this condition either and the patient still being able to move his eye freely in spite of partial deformation. In this condition, easy alignment of the contact glass with the eye is possible. Once the desired adjustment position is achieved, the distance between the contact glass and the patient's eye is reduced somewhat further, causing the annular gap to be closed by the cornea of the eye and causing the eye to be vacuum-fixed relative to the contact glass.

The curved surface imposed upon the eye as the desired shape by the anterior lens surface can be selected in an application-dependent manner. In particular, aspherically curved surfaces are also possible which allow optical imaging errors to be minimized when introducing treatment laser radiation. The anterior lens surface may also be spherical, with a radius of from 5-30 mm. A radius of slightly less than that of the human cornea, i.e. between 15 and 25 mm, for example, is particularly preferred. This sphericity is possible without a problem due to the design according to the invention, because contrary to the prior art in the form of US 2001/0021844 A1, there is no danger of the eye's cornea occluding the vacuum suction channel such that the contact glass is fixed only incompletely to the eye.

The suction orifices surrounding the anterior surface of the lens in a ring shape are preferably provided as part of a suction channel. Further, the suction orifices are favorably provided such that, when the eye fully contacts the anterior surface of the lens, they are not yet covered by the eye's cornea so that suction is not yet effected as a result. In this condition, precise positioning of the contact glass relative to the eye is possible. It is only when the contact glass is pressed further onto the eye that the eye's cornea also covers the suction orifices, whereby the vacuum fixation becomes effective.

This design of the contact glass may be achieved, for example, by the annular region in which the suction orifices located being angled relative to the optical axis and/or having a concave curvature, e.g. one which is slightly smaller than the curvature of the eye's cornea. Of course, the anterior surface of the lens may also be concave.

A convenient and particularly easy-to-produce structure of the contact glass consists in that the anterior surface of the lens is formed on a lens body held in a mount, with the suction orifices being provided in the mount. The just mentioned two-step mounting, wherein the vacuum mounting is effective only when the contact glass, in its adjusted condition, is pressed further onto the eye, can then be achieved simply if the axially forward contour of the mount does not protrude with respect to a curvature which the eye's cornea has when the eye is in full contact with the anterior surface of the lens, or if said contour even recedes relative to said curvature. That part of the mount which comprises the suction orifices will conveniently be seamlessly contiguous with the anterior surface of the lens.

Particularly easy production is achieved if the suction channel is formed between the mount and the lens body and individual channels extend from the suction channel through the wall of the mount and into the suction orifices. The suction channel may then be, for example, an annular gap between the mount and the lens body, which gap is covered by a wall of the mount on the patient's side, said wall extending from an exteriorly located edge of the mount to the edge of the anterior surface of the lens. Breakthroughs in this wall form individual channels and, thus, form the suction orifices.

The number of suction orifices is not fixed to a specific figure but will have to be selected according to the conditions of manufacture. The shape of the suction orifices may also be selected according to conditions of manufacture; in particular, they may be round, oval or rectangular. In order to prevent injuries of the eye's cornea, care should be taken, of course, to remove burrs during manufacture.

The curved surface imposed upon the eye as the desired shape by the anterior lens surface can be selected in an application-dependent manner. In particular, aspherically curved surfaces are also possible which allow optical imaging errors to be minimized when introducing treatment laser radiation.

The contact glass according to the invention allows the natural shape of the cornea to be maintained with the contact glass placed thereon, which is particularly convenient for patients. With a suitable curvature of the anterior lens surface, the eye is placed in contact with the contact glass with minimal deformations. The anterior lens surface may be spherically curved in this case, having a radius of curvature of 5-30 mm; a radius which is slightly greater than that of the human eye is preferred and therefore lies in the range from 15-25 mm.

The annularly arranged suction orifices effectively prevent parts of the eye's cornea being sucked into the upper part of the suction channel and thus partially occluding the latter. As a consequence, introduction of the vacuum into the suction channel is uncritical, because the entire suction channel is effective at all times and, in particular, the vacuum connector cannot be occluded by the eye's cornea.

The contact glass according to the invention enables particularly easy placement of the contact glass onto the eye's cornea, in particular if the curved surface of the anterior lens surface has a slightly flatter curvature than the eye's cornea. When approaching the contact glass, only the central region of the eye's cornea, i.e. the corneal vertex, touches the anterior lens surface. As placement progresses, the eye's cornea gradually contacts the full anterior lens surface, with the suction orifices still not being covered in this condition either and the patient still being able to move his eye freely in spite of partial deformation. In this condition, easy alignment of the contact glass with the eye is possible. Once the desired adjustment position is achieved, the distance between the contact glass and the patient's eye is reduced somewhat further, causing the annular gap to be closed by the cornea of the eye and causing the eye to be vacuum-fixed relative to the contact glass.

It has turned out that suction of the conjunctiva (sclera) to the vacuum fixing means should be avoided during vacuum fixing of an ophthalmic contact glass, because otherwise insufficient fixing of the eye's cornea on which surgery is to be performed may occur. Thus, said vacuum fixation preferably acts exclusively on the cornea and not on the sclera of the eye.

Regardless of how the contact glass is designed in other respects and in particular regardless of the design of the means for vacuum fixation, it is convenient to provide a contact glass for ophthalmic surgery comprising an anterior lens surface designed to be placed on the eye and means for vacuum fixture of the contact glass to the eye, and which is further characterized in that a coding element encoding a geometric or optical parameter of the contact glass is provided on the contact glass. The geometric or optical parameter is conveniently the diameter of the anterior lens surface. The coding element is favorably attached to the contact glass in a manner allowing a user, i.e. an eye surgeon, to recognize the desired geometric or optical parameter, e.g. the desired diameter of the anterior lens surface, from the outside. A suitable coding element is a bar code, a number or letter code or even a geometric or color code, for example. A contact glass bearing a color mark is particularly preferred, the color mark being assigned to the diameter of the anterior lens surface or to another geometric or optical parameter of the contact glass. If the contact glass is produced in two parts, i.e. from a lens body comprising the anterior lens surface as well as a mount holding the lens body, it will be favorable to arrange the coding element on the mount. In the case of a color code, the mount itself can be colored, for example.

Of course, a variant is also possible including an information carrier and a device for wireless reading and/or modification of the information stored thereon. The transmission of information may be effected by electromagnetic signals (e.g. in the radio frequency range between 100 kHz and 1 GHz, or as described in WO 2005039462 A1).

The device for wireless reading and/or modification of the stored information, which device communicates with the contact glass, may comprise a transmitter and a receiver. By its signal, the transmitter can transmit energy to the information memory, which information the latter uses in turn to emit information stored by it in the form of a response signal.

It is possible to modify the information stored in the information memory by means of a signal from the transmitter. (When transmitting information again from the accessory part to the product, the modified information will then be transmitted.) The information memory and the mount may constitute a mechanical unit, and it is possible to sterilize the accessory part together with the integrated information memory.

In order to allow a user to select a contact glass having the desired parameters, the code is advantageously provided as an optically perceivable code, allowing a surgeon to select the desired contact glass in a quick and unerring manner.

Use of the above-described coding element is particularly advantageous, of course, in a contact glass of the type described hereinbefore or hereinafter.

BRIEF DESCRIPTION OF THE DRAWINGS

The invention will be explained in more detail below, by way of example and with reference to the Figures, wherein:

FIGS. 3 and 4 depict a contact glass for the laser processing device of FIG. 1, with FIG. 3 being a top view and FIG. 4 being a sectional view;

FIGS. 5 to 8 are schematic sectional views of contact glasses similar to that of FIG. 3/4;

FIG. 9 is a sectional view of a further variant of a contact glass for the laser processing device of FIG. 1;

FIG. 10 is a plan view of the contact glass of FIG. 9 from below (with respect to FIG. 3) and FIG. 11 is a representation similar to FIG. 10 depicting a further construction of a contact glass.

DETAILED DESCRIPTION

Figure 1:
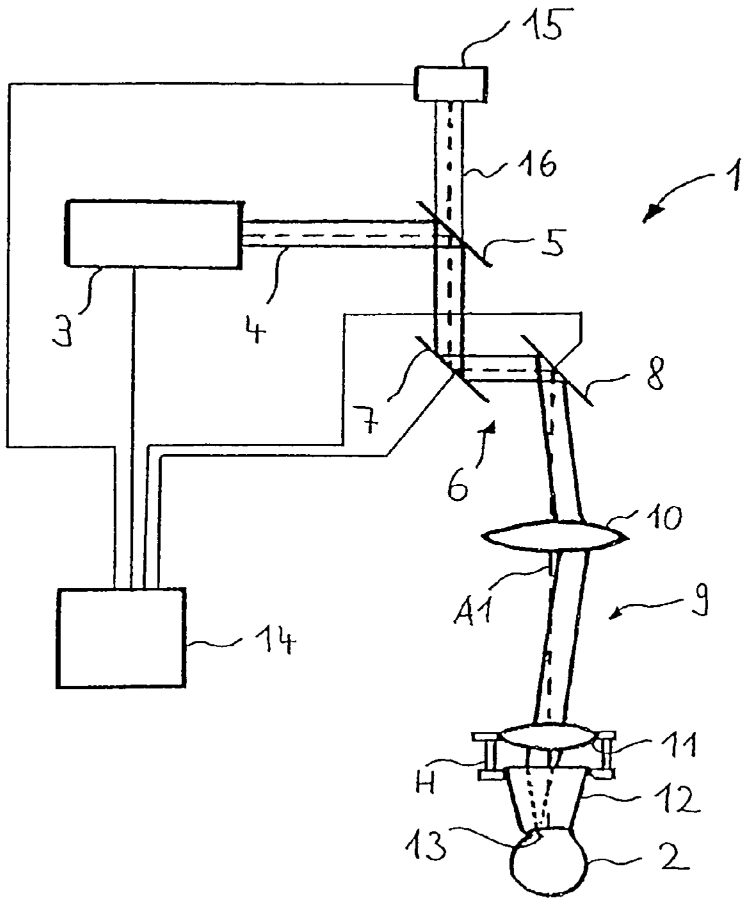
FIG. 1 is a schematic representation of a laser processing device for ophthalmic surgery.

FIG. 1 shows a treatment device for an ophthalmic method similar to those described in EP 1159986 A1 and U.S. Pat. No. 5,549,632. The treatment device 1 of FIG. 1 serves to perform correction of an eyesight defect on a patient's eye 2 according to the known femtosecond LASIK method. For this purpose, the treatment device 1 has a laser 3 which emits pulsed laser radiation. The pulse duration is within the femtosecond range, for example, and the laser radiation acts by means of non-linear optical effects in the cornea, as described above. The treatment beam 4 emitted by the laser 3 along an optical axis A1 is incident on a beam splitter 5 which transmits the treatment beam 4 to a scanning unit 6. The scanning unit 6 comprises two scanning mirrors 7 and 8 which are rotatable about mutually orthogonal axes such that the scanning unit 6 two-dimensionally deflects the treatment beam 4. Adjustable projection optics 9 focus the treatment beam 4 onto or into the eye 2. The projection optics 9 comprise two lenses 10 and 11. The treatment device 1 is a laser processing device.

Arranged following the lens 11 is a contact glass 12 which is securely connected to the lens 11, and thus to the beam path of the treatment device 1, via a holder H. The contact glass 12, which will be explained in more detail below, contacts the cornea of the eye 2. The optical combination of the treatment device 1 with the contact glass 12 fixed thereto causes the treatment beam 4 to be focused in a focus 13 located within the cornea of the eye 2.

Like the laser 3 and the projection optics 9, the scanning unit 6 is controlled by a control device 14 via control lines (not specifically designated). The control device 14 determines the position of the focus 13 both transverse to the optical axis A1 (by the scanning mirrors 7 and 8) and in the direction of the optical axis A1 (by the projection optics 9).

The control device 14 further reads out a detector 15 which reads out radiation scattered back from the cornea and passing through the beam splitter 5 as return radiation 16. The detector 15 allows very precise control of the operation of the laser 3.

The contact glass 12 ensures that the cornea of the eye 2 obtains a desired specified shape. Due to the cornea 17 contacting the contact glass 12, the eye is located in a predetermined position with respect to the contact glass 12 and thus to the treatment device 1 connected thereto.

Figure 2:
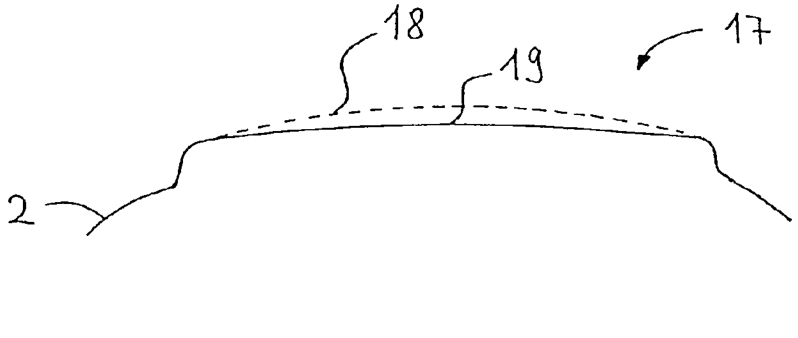
FIG. 2 is a schematic view of a patient's cornea.

This is schematically illustrated in FIG. 2 which shows a sectional view of the eye's cornea 17. In order to achieve exact positioning of the focus 13 in the eye's cornea 17, the curvature of the eye's cornea 17 has to be considered. The cornea 17 has an actual shape 18 which differs from patient to patient. The adapter 12 contacts the eye's cornea 17 such that it deforms the latter towards a desired shape 19. The exact profile of the desired shape 19 depends on the curvature of the anterior lens surface of the contact glass that faces towards the eye 2. Known geometric and optical conditions for introducing and focusing the treatment beam 4 into the cornea 17 are given by the adapter 12. Since the cornea 17 contacts the contact glass 12, which is in turn stationary with respect to the beam path of the treatment device 1 due to the holder H, exact three-dimensional positioning of the focus 13 is achieved by controlling the scanning unit 6 as well as the adjustable projection optics 9.

FIGS. 3 and 4 show an embodiment of the contact glass 12 in detail; FIG. 4 is a sectional view, FIG. 3 is a front view of the contact glass 12 (bottom view in FIG. 4), i.e. within view of the patient. The contact glass 12 has a two-part design and consists of a lens body 22, which is secured in a mount 37, e.g. glued in at a gluing location 43. The lens body consists of glass or a medically approved plastic material, e.g. PMMA or polycarbonate. These substances are also suitable for the mount, which may be additionally made of polyurethane or silicone rubber. By pressing the contact glass 12 onto the eye's cornea 17, the anterior lens surface 29 of the lens body 22 held in the mount 37 imparts the desired shape 19 to the eye's cornea 17.

In order to provide the vacuum, the mount 37 comprises a port 38, which includes a Luer lock connection 39 as well as a vacuum supply line 40 extending inside the port. The supply line 40 terminates laterally of the lens body 22 above an attachment ring 41 of the mount 37. An annular gap 41 is formed between an inner ring surface 46 of the attachment ring 41 and the lens rim 47, which is frustoconical in this embodiment, said annular gap 41 being in communication with the supply line 40 and acting as a suction channel by which a vacuum can be applied in a ring shape on the eye's cornea. Thus, the contact glass 12 is fixed to the eye by a vacuum at the Luer lock connection 39 such that the cornea contacts the anterior lens surface 29 by mechanical pressure, thus achieving the desired shape 19.

The attachment ring 41 protrudes from the anterior lens surface 29 relative to the optical axis A1.

When placing the contact glass on the eye's cornea, contact is established first between the anterior lens surface 29 and the corneal vertex. As the application of the eye's cornea to the anterior lens surface 29 progresses, contact with the eye's cornea is established in an increasingly large surface region of the anterior lens surface. When the eye's cornea fully contacts the anterior lens surface 29, no contact is established yet between the axially foremost contour line of the attachment ring 41 and the eye's cornea, due to the increasing curvature in the peripheral region of the eye's cornea, so that the suction channel provided by the annular gap 44 is not yet closed by the eye's cornea. Accordingly, it is still possible in this condition to adjust the eye, which is in contact with the anterior lens surface 29, such that the optical axis A1 is located exactly as desired, e.g. coincides with the axis of vision. Only upon pressing the contact glass and the eye closer together does the eye's cornea also contact the axially foremost contour line 45 of the attachment ring 41, whereby the suction channel at the annular gap 44 is closed at the suction orifices 45 and the contact glass 12 is fixed to the eye.

The mount 37 is accordingly designed such, with respect to the attachment ring 41, that the axially foremost contour line 45 of the attachment ring 41 does not protrude relative to that of a curved surface defined by the curvature of the eye when the eye's cornea is in full contact with the anterior lens surface 29. In one embodiment, the attachment ring 41 is located exactly in the imaginary extension of the curved surface. For simplification, the curvature of the anterior lens surface 29 can also be used as a reference.

Tapering off from the eye, the shape of the annular gap 44 reliably prevents parts of the cornea being sucked into the region of the supply line 40 and thereby at least partially clogging or covering it. Clogging of the suction channel 44 is also avoided, so that ring-shaped application of the vacuum is ensured.

FIGS. 5 to 8 schematically show different embodiments of the geometry of the lens body 22 and mount 37. Any elements already present in the construction of FIGS. 3/4 are designated with the same reference symbols, so that reference is made here also to the description pertaining to FIGS. 3 and 4.

The contact glass 12 again comprises the lens body 22 which is held in the mount 37. The lens body 22 is limited by an entrance surface 23 and the anterior lens surface 29. The shape of a piano-concave lens is preferred, with the curvature of the concave anterior lens surface 29 particularly preferably corresponding to the human cornea or having a somewhat flatter curvature. However, other shapes are also possible. In particular, the anterior lens surface 29 may also be aspherical so as to minimize optical imaging errors.

The mount 37 encloses the lens body 22 on part of its circumference, thus forming a connecting surface between the lens body 22 and the mount element 37 substantially along a cylindrical shell. The annular gap 44 serving as a suction channel is formed between the rim of the lens body 22 and the attachment ring 41 of the mount 37 and the rim 47 of the anterior lens surface 29 of the lens body 22.

Now, in order to provide the annular gap, as shown in FIGS. 5 to 8, either the internal ring surface 46 of the attachment ring 41 and/or the lens rim 47 may be conical, i.e. may extend obliquely with respect to the optical axis A1. In the embodiment of FIG. 5, the lens rim 47 is conical and the internal ring surface 46 is cylindrical. Further, it is clearly evident that the attachment ring 41 does not protrude, but rather recedes somewhat, with respect to the already mentioned curved surface K, which is predetermined by the curvature of the contacted cornea of the eye. The construction of FIG. 5 has the advantage that a simple, substantially tubular mount 37 can be used. Further, the diameter of the anterior lens surface 29 is smaller than that of the entrance surface 23.

The opposite case is shown in FIG. 6, wherein the lens rim 47 is cylindrical, while the internal ring surface 46 is conical, with the cone now opening towards the curved surface K. Also, the attachment ring 41 extends exactly as far as the curved surface K here.

In the construction according to FIG. 7, both the lens body 22 at the lens rim 47 (tapering towards the eye) and the internal ring surface 46 (expanding towards the eye) are conical. Further, the axially foremost contour line of the attachment ring 41 recedes with respect to the curved surface K. This has the advantage that full adjustment of the eye with respect to the contact glass 12 is possible and the suction channel is closed by the contact of the eye's cornea only upon applying additional mechanical pressure.

Finally, FIG. 8 shows a construction similar to that of FIG. 7. However, both the internal ring surface 46 and the lens rim 47 conically taper towards the eye. In this case, it is advantageous if the contact surface of the contact glass 12 on the eye has a smaller diameter, while the entrance surface 23 has a large diameter.

FIG. 9 shows a detail of a further variant of the contact glass 12 in a sectional view. This is a modification of the contact glass of FIGS. 3 and 4; therefore, like elements are identified by like reference symbols. The contact glass 12 has a two-part design and consists of the lens body 22, which is secured in a mount 37, e.g. by gluing. The lens body 22, which may be made of glass, for example, has the planar entrance surface 23, at which the treatment radiation from the laser treatment device 1 is supplied, and the anterior lens surface 29, which is located opposite, on the patient's side, and is adapted to the curvature of the human cornea. By pressing the contact glass 12 onto the eye's cornea 17, the anterior lens surface 29 of the lens body 22 held in the mount 37 imparts the desired shape 19 to the eye's cornea 17. The lens body 22 consists of glass or of medically approved plastics, such as PMMA or polycarbonate. These materials are also suitable for the mount, which may be additionally made of polyurethane or silicone rubber.

In order to provide the vacuum, the mount 37 comprises the port 38 which is provided with the connecting port 39, with a vacuum tube fitted thereon, as well as the vacuum supply line 40 extending inside the port 38. The supply line 40 terminates laterally of the lens body 22 above the attachment ring 41 of the mount 37.

With its surface located on the patient's side (viewed from below in the illustration of FIG. 3), the attachment ring 41 continues the curvature of the anterior lens surface 29 such that the axially outermost contour of the attachment ring 41 is located, in the form of the lower edge 42, in an extension of the curvature of the anterior lens surface 29. The suction surface 43 is formed between said edge 42 and the outer edge of the anterior lens surface 29.

The suction surface 43 covers the annular suction channel 44, which is formed by a gap between the mount 37 and the lens body 22 in this embodiment. In principle, however, it would also be possible for the suction channel to be located completely within the material of the mount 37. In the embodiment shown in FIG. 9, the suction surface 37 is thus formed by a wall extending from the outermost edge 42 of the attachment ring 41 to the edge of the anterior lens surface 29. In the suction surface 43, i.e. within said wall, suction orifices 45 are formed, which constitute the patient-side ends of individual channels 46 whose other ends terminate in the suction channel 44.

Thus, through the vacuum supply line 40, a vacuum applied to the vacuum connection 39 reaches the vacuum channel 44, where it acts on the eye's cornea by means of the suction orifices 45 surrounding the anterior lens surface 29 in a ring-shaped manner.

Since the suction surface 43 preferably continues the curvature of the anterior lens surface 29 in a smooth manner (with a continuation of a spherically curved surface being possible, but also an aspherical curvature or a curvature with a radius of curvature which differs from that of the anterior lens surface 29 and is either greater or smaller), there is a largely smooth transition from the anterior lens surface 29 to the suction surface 43 on the whole. In any case, the transition has no sharp edges, but consists, at the most, of an annular boundary at which the curvature or inclination changes.

FIG. 10 shows the contact glass 12 of FIG. 9 in a view from the patient's side, i.e. from below in FIG. 9. As is clearly visible, the suction orifices 45 are oval here and surround the anterior lens surface 29 externally of a boundary 147 between the mount 37 and the lens body 22 in the region of the annular suction surface 43.

FIG. 11 shows a modified design, wherein the suction orifices 45 have a different geometric shape, namely the shape of half-ovals providing an arcade-shaped structure of the suction orifices 45. The vacuum connection is also differently designed here, namely as a Luer lock connection.

The diameter of the annular suction surface 43 and thus also of the anterior lens surface 29 is preferably selected in a patient-dependent manner. Thus, different contact glasses 12 having different diameters of the anterior lens surface 29 and thus different diameters of the annular suction surface 43 are kept in store for one single treatment device, so that the suction orifices 45 are definitely in place on the cornea of the patient receiving treatment, thus ensuring optimal suction. This avoids suction of the conjunctiva in the region of the suction surface 43. In order to make it easier for the user to distinguish between different contact glasses 12, e.g. contact glasses having different diameters of the anterior lens surface 29 (and thus of the suction surface 43) or having different radiuses of curvature, a code is optionally provided in the region of the mount 37. It is particularly advantageous here to dye the entire mount.

Alternatively, the mount is provided with an RFID chip and the device 1 is provided with a corresponding transmitter/receiver unit. The range of the transmitter/receiver unit is confined to a narrow space (e.g. 10 cm). When the contact glass is placed in the mount, the device 1 verifies, evaluates and, if necessary, modifies the stored information. Such modification is advantageous in disposable contact glasses, because it allows avoidance of repeated use.

Specifically, the RFID chip may be integrally cast. The RFID chip may be sterilized individually or in connection with the entire contact glass. A glass sterilization using ethylene dioxide (ETO) is preferable. The treatment device 1 is equipped with an RFID transmitter/receiver and reads the stored information (e.g. of an ID or use code). Multiple use is prevented either in that the same code of use is accepted only once by the respective device 1, i.e. only one single laser therapy is activated by this ID code (as described also in US 2006/0129140), or the device 1 modifies the information in the chip such that a second or $n^{th}$ use is ruled out even with other devices.

Of course, this principle may be employed for any combinations of an accessory part and a medical device.

For easier observation of the patient's eye when using the contact glass 12, it is possible to irradiate light from a light source through the mount 37 to the site of treatment. This is described, for example, in DE 10353264 A1. The suction surface 43 being interrupted merely in the region of the suction orifices 45 considerably facilitates coupling-in of the radiation and it is no longer required to use the optical means described in DE 10353264 A1, which are provided in order to compensate for the optical effect of an annularly opened suction channel.

When placing the contact glass on the eye's cornea, contact is established first between the anterior lens surface 29 and the corneal vertex. As the application of the eye's cornea to the anterior lens surface 29 progresses, contact with the eye's cornea is established in an increasingly large surface region of the anterior lens surface. When the eye's cornea fully contacts the anterior lens surface 29, no contact is established yet between the axially foremost contour line of the attachment ring 41 and the eye's cornea, due to the increasing curvature in the peripheral region of the eye's cornea, so that the suction orifices 45 are not yet covered by the eye's cornea. Accordingly, it is still possible in this condition to adjust the eye, which is in contact with the anterior lens surface 29, such that the optical axis A1 is located exactly as desired, e.g. coincides with the axis of vision. Only upon pressing the contact glass and the eye closer together does the eye's cornea also contact the axially foremost contour line 42 of the attachment ring 41, whereby the suction channel 44 is closed at the suction orifices 45 and the contact glass 12 is fixed to the eye.

For example, the mount 37 is designed such, with respect to the attachment ring 41, that the axially foremost contour line of the periphery 42 of the attachment ring 41 does not protrude relative to that of a curved surface defined by the curvature of the eye when the eye's cornea is in full contact with the anterior lens surface 29. In one embodiment, the periphery 42 is located exactly in the imaginary extension of the curved surface. For simplification, the curvature of the anterior lens surface 29 can also be referred to.

Of course, the geometric designs described herein can also be advantageously used individually or in other combinations not explicitly shown or described.

The invention claimed is:

1. A contact glass adapter for ophthalmic surgery, comprising a lens body having a front lens surface for placement onto a cornea of an eye, the cornea of the eye having a corneal diameter, a lens mount being integral with the lens body or connected to the lens body, the contact glass adapter having a anterior end and a posterior end, the posterior end being farthest from the eye when the contact glass is applied to the eye and the anterior end being nearest to the eye when the contact glass is applied to the eye, wherein a multiplicity of suction orifices is defined in the lens mount, for providing a vacuum on the cornea of the eye through the multiplicity of suction orifices, wherein the multiplicity of suction orifices surround the front surface of the lens body and are bordered by the anterior contour of the lens mount, wherein the lens mount extends circumferentially around the lens body and is structured such that a complete circumference of the lens mount does not contact the cornea when the front lens surface is in full contact with the cornea.

2. The contact glass adapter as claimed in claim 1, wherein the front lens surface has a periphery and a suction channel is provided between the lens body and the lens mount, which suction channel annularly surrounds the periphery of the front lens surface and to which the suction orifices open.

3. The contact glass adapter as claimed in claim 2, wherein the suction channel has a multiplicity of individual channels, extending through a wall of the mount and terminating in the multiplicity of suction orifices.

4. The contact glass adapter as claimed in claim 1, wherein the front lens surface defines a concave curvature and wherein the suction orifices are located on a curved annular surface.

5. The contact glass adapter as claimed in claim 1, wherein the suction orifices are one of round, oval and rectangular.

6. The contact glass adapter as claimed in claim 1, further comprising, a port for coupling illumination radiation into the lens mount to illuminate the eye through the region of the multiplicity of suction orifices.

7. The contact glass adapter as claimed in claim 1, wherein the front lens surface is aspherical.

8. The contact glass adapter as claimed in claim 1, further comprising a coding element, for encoding a geometric or optical parameter of the contact glass.

9. The contact glass adapter as claimed in claim 8, wherein the coding element codes the diameter of the front lens surface.

10. The contact glass adapter as claimed in claim 8, wherein the coding element comprises an RFID chip which stores an ID code wherein the RFID chip is adapted to communicate with a transmitting/reading unit provided in a treatment device.

11. A system comprising a contact glass as claimed in claim 10 and a treatment device comprising the transmitting/reading unit, wherein the transmitting/reading unit reads out the ID code stored in the RFID chip, and wherein the treatment device is adapted to perform ophthalmic surgery only in the case of an preselected ID code being present.

12. The system as claimed in claim 11, wherein the transmitting/reading unit is operably connected to an ID code memory unit in which ID codes of already used contact glasses are stored to make sure that each contact glass is used only once.

13. The system as claimed in claim 11, wherein the transmitting/reading unit modifies the ID code in the RFID chip after one use of the contact glass.

14. The contact glass adapter as claimed in claim 1, wherein the suction orifices are structured such that the vacuum acts on the cornea of an eye.

15. A contact glass adapter for ophthalmic surgery, comprising a lens body having an anterior lens surface for placement onto a cornea of an eye, the cornea of the eye having a corneal diameter, a lens mount being integral with the lens body or connected to the lens body, the contact glass adapter having a anterior end and a posterior end, the posterior end being farthest from the eye when the contact glass is applied to the eye and the anterior end being nearest to the eye when the contact glass is applied to the eye, wherein an annular gap is defined by a space between the anterior lens mount and the anterior lens body for providing a vacuum on the cornea of the eye through the annular gap, and wherein the annular gap surrounds the anterior surface of the lens body and is bordered by the anterior contour of the lens mount, wherein the lens mount extends circumferentially around the lens body and is structured such that a complete circumference of the lens mount does not contact the cornea when the front lens surface is in full contact with the cornea.

16. The contact glass adapter as claimed in claim 15, wherein the front lens surface is concave for fitting on the eye, wherein said annular gap, together with the contacted eye, acts as a suction channel for applying a vacuum for fixing the contact glass to the eye, with the mount being structured such that the suction channel between the annular gap and the eye is not yet closed when the eye is placed in full-surface contact with the front lens surface.

17. The contact glass adapter as claimed in claim 16, wherein the front lens surface is concave corresponding to a curved surface.

18. The contact glass adapter as claimed in claim 17, wherein an internal surface of the mount, which limits the annular gap, and/or a rim surface of the lens body limiting the annular gap, comprises a frusto-conical surface extending obliquely with respect to the optical axis.

19. The contact glass adapter as claimed in claim 16, wherein the annular gap becomes narrower as distance from the anterior end increases.

20. The contact glass adapter as claimed in claim 19, wherein an end of the annular gap facing away from the anterior end tapers at an angle of equal to or less than 90 degrees.

21. The contact glass adapter as claimed in claim 15, further comprising a port for coupling illumination radiation into the lens mount to illuminate the eye through the region of the multiplicity of suction orifices.

22. The contact glass adapter as claimed in claim 15, wherein the front lens surface is aspherical.

23. The contact glass adapter as claimed in claim 15, further comprising a coding element encoding a geometric or optical parameter of the contact glass.

24. The contact glass adapter as claimed in claim 23, wherein the coding element codes the diameter of the front lens surface.

25. The contact glass adapter as claimed in claim 23, wherein the coding element comprises an RFID chip which stores an ID code, wherein the RFID chip is adapted to communicate with a transmitting/reading unit provided in a treatment device.

26. A system comprising a contact glass as claimed in claim 25 and a treatment device comprising the transmitting/reading unit, wherein the transmitting/reading unit reads out the ID code stored in the RFID chip, and wherein the treatment device is adapted to perform ophthalmic surgery only in the case of a preselected ID code being present.

27. The system as claimed in claim 26, wherein the transmitting/reading unit is operably connected to an ID code memory unit in which ID codes of already used contact glasses are stored to make sure that each contact glass is used only once.

28. The system as claimed in claim 26, wherein the transmitting/reading unit modifies the ID code in the RFID chip after one use of the contact glass.

29. The contact glass adapter as claimed in claim 15, wherein the annular gap is structured such that the vacuum acts on the cornea of an eye.

* * * * *

UNITED STATES PATENT AND TRADEMARK OFFICE

CERTIFICATE OF CORRECTION

PATENT NO. : 8,944,601 B2
APPLICATION NO. : 12/064575
DATED : February 3, 2015
INVENTOR(S) : Muehlhoff It is certified that error appears in the above-identified patent and that said Letters Patent is hereby corrected as shown below:

Title Page:

Under (75) Inventors: Delete “Bad Berka” and insert --Jena--

Signed and Sealed this
Eleventh Day of August, 2015

Michelle K. Lee
*Director of the United States Patent and Trademark Office*